(12) United States Patent
Biedermann et al.

(10) Patent No.: US 7,547,325 B2
(45) Date of Patent: Jun. 16, 2009

(54) SPACE KEEPER WITH ADJUSTABLE AXIAL LENGTH

(75) Inventors: Lutz Biedermann, VS-Villingen (DE); Jürgen Harms, Karlsruhe (DE); Peter Ostermann, Bocholt (DE)

(73) Assignee: Biedermann Motech GmbH (DE)

( * ) Notice: Subject to any disclaimer, the term of this patent is extended or adjusted under 35 U.S.C. 154(b) by 523 days.

(21) Appl. No.: 10/250,489

(22) PCT Filed: Aug. 2, 2002

(86) PCT No.: PCT/EP02/08648

§ 371 (c)(1),
(2), (4) Date: Jul. 2, 2003

(87) PCT Pub. No.: WO03/013399

PCT Pub. Date: Feb. 20, 2003

(65) Prior Publication Data

US 2004/0049271 A1 Mar. 11, 2004

(30) Foreign Application Priority Data

Aug. 3, 2001 (DE) ................................. 101 38 079

(51) Int. Cl.
*A61F 2/44* (2006.01)
(52) U.S. Cl. .................................................. 623/17.16
(58) Field of Classification Search ............... 623/11.11, 623/16.11, 17.11–17.16, 18.11, 23.45–23.47; 606/60, 61; 403/109.1–109.4, 238, 377, 403/378, 379.3, 43–48
See application file for complete search history.

(56) References Cited

U.S. PATENT DOCUMENTS

| | | | | |
|---|---|---|---|---|
| 2,678,226 A | * | 5/1954 | White | 403/46 |
| 4,553,273 A | * | 11/1985 | Wu | 623/23.45 |
| 5,702,455 A | * | 12/1997 | Saggar | 623/71.15 |
| 6,200,348 B1 | | 3/2001 | Biedermann et al. | 623/17.11 |
| 6,454,806 B1 | * | 9/2002 | Cohen et al. | 623/17.15 |
| 6,719,796 B2 | * | 4/2004 | Cohen et al. | 623/17.15 |

FOREIGN PATENT DOCUMENTS

| | | |
|---|---|---|
| EP | 0 977 528 B1 | 2/2000 |
| EP | 1 080 703 A2 | 3/2001 |
| WO | WO 95/25485 | 9/1995 |
| WO | WO 99/39665 | 8/1999 |
| WO | WO 9939665 * | 8/1999 |
| WO | WO 99/63913 | 12/1999 |

* cited by examiner

*Primary Examiner*—Anu Ramana
(74) *Attorney, Agent, or Firm*—Christie Parker & Hale, LLP.

(57) ABSTRACT

A space keeper for insertion between two vertebrae which has a variable axial length is provided. The space keeper possesses a sleeve-like first member (2) and a second member (3) guided in the latter and movable relative to the first member in the axial direction for adjusting an overall length. In order that adjustability during operating is facilitated the two members (2, 3) are connected to one another by a lever (7, 8), wherein one centre of motion (16) of the lever is connected to one member (3) and the other centre of motion (18) is connected in terms of action to the other member (2).

11 Claims, 3 Drawing Sheets

SPACE KEEPER WITH ADJUSTABLE AXIAL LENGTH

BACKGROUND OF THE INVENTION

The invention relates to a space keeper for inserting between two vertebrae, the space keeper having an adjustable axial length and a sleeve-like first member and a second member guided in the latter and movable in the axial direction relative to the first member for setting an overall length.

A space keeper of this type is known from EP 0 977 528 A1. In this the two members in the telescoped position are inserted between two vertebrae and then pulled apart by hand to the desired length and then locked in the extended position.

SUMMARY OF THE INVENTION

It is the object of the invention to provide a space keeper of the type described at the outset in which the operating surgeon can manage the adjustment to the desired length in the most simple manner.

This task is solved by a space keeper of the type described at the outset which is characterized in that the two members are connected to one another by a lever one of whose centers of motion is connected to one member and whose other centre of motion is connected to the other member.

Refinements of the invention are identified in the subsidiary claims.

BRIEF DESCRIPTION OF THE DRAWINGS

Further features and functions of the invention emerge from the description of embodiments with reference to the figures. In the figures.

DETAILED DESCRIPTION

Figure 1:
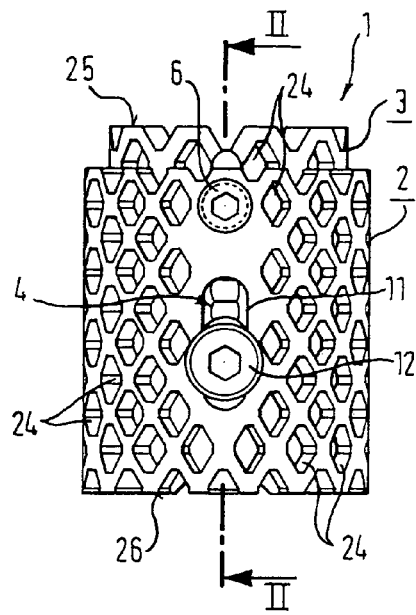
FIG. 1 a side view of the space keeper in the contracted position.

As may be seen best in FIG. 1 a space keeper 1 comprises a sleeve-like first member 2 and a sleeve-like second member 3 guided in the former. The two members can be pushed into one another to a maximum extent as shown in FIGS. 1 and 2 and be moved apart to a maximum length as shown in FIG. 3.

Figure 2:
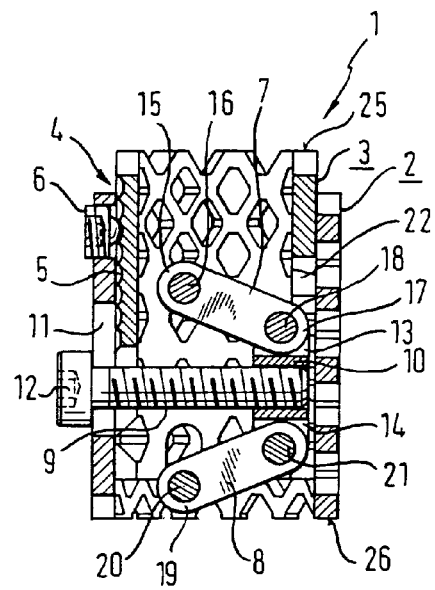
FIG. 2 a section along the line II/II in FIG. 1.
Figure 3:
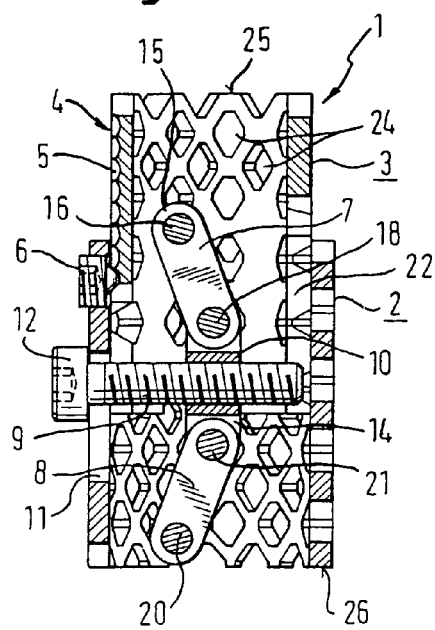
FIG. 3 the same section as in FIG. 2 but this time with the space keeper pulled apart to its maximum length.

As may be seen in FIGS. 1 to 3 the inner second member 3 has on its outer wall facing towards the outer first member 2 a section with a catch 4 extending in the axial direction having a plurality of depressions 5 arranged adjacent to one another in the axial direction and bounding one another and the outer first member 2 has a fixing member 6 which can be brought into engagement with the catch. The fixing member serves the purpose of locking the two members in a desired position.

Figure 4:
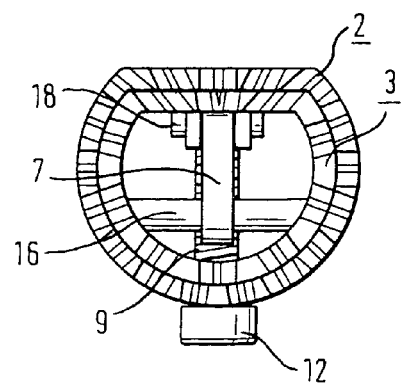
FIG. 4 a plan view onto the object shown in FIG. 1.

As may be seen best in FIGS. 2 and 4 the spacer 1 has a lever device for adjusting the axial position of the two members relative to one another. In the first embodiment this comprises a first lever arm 7, a second lever arm 8, a setting screw 9 and a threaded sleeve 10. As may be seen best in FIG. 2 the outer first member 2 has a recess 11 on the side whose lateral extension is smaller than the diameter of the head 12 of the setting screw 9 as may be seen best in FIG. 1. The setting screw 9 is inserted in the manner shown in FIG. 2 into the interior of the sleeve-like members at right angles to the axial direction. The threaded sleeve 10 is screwed onto the screw. On both sides extending in the axial direction of the sleeve it has shoulders 13, 14. The shoulder 13 serves to connect to the first lever arm 7. The lever arm is mounted pivotably about a shaft 16 by its first end 15 by means of this shaft mounted on two opposite points of the wall of the second member 3. The shaft extends perpendicular to the longitudinal axis of the space keeper. At its second end 17 opposite the connection to the shaft 16 the first lever arm is connected pivotably about a shaft 18 to the shoulder 13 via a pin or shaft 18. The pin or shaft 18 extends parallel to the shaft 16.

As illustrated in FIG. 2 the second lever arm 8 viewed about the setting screw 9 is constructed or arranged symmetrically relative to the first lever arm 7. At its first end 19 correspondingly located opposite end 15 the lever arm is mounted via a shaft 20 to pivot about the latter. The shaft 20 is mounted on the side in the side walls located opposite one another of the first member 2 and extends parallel to the shaft 16. At its end located opposite the end 19 the second lever arm is connected pivotably about a shaft 21 to the shoulder 14 by means of a pin or shaft 21.

As may be seen in FIGS. 1 and 2 the recess 11 is constructed as an oblong hole extending in a direction parallel to the longitudinal axis of the spacer. The oblong hole is positioned in such a way that the setting screw 9 is movable back and forth therein to such an extent that the screw is movable back and forth in the oblong hole from the compressed position shown in FIG. 2 to the extended position shown in FIG. 3.

In operation the space keeper in the contracted position shown in FIG. 2 with minimal length in the axial direction is inserted between the vertebrae. The length is then set to a desired length by engaging by means of a screwdriver in a corresponding slit or hexagonal opening of the head 12 of the setting screw 9 in that the setting screw 9 is turned in such a way that the threaded sleeve 10 is moved from the most extreme position shown in FIG. 2, in which the threaded sleeve is located at the free end of the setting screw 9, towards the head. In doing so the two levers 7, 8 are moved from their retracted position into a maximum extended position shown in FIG. 3. In this way the two sleeve-like members 2 and 3 are moved from the contracted position shown in FIG. 2 into the expanded position shown in FIG. 3 or any intermediate position. Due to the screw guidance between the setting screw 9 and threaded sleeve 10 the two members remain initially in the position reached by turning the setting screw 9. As soon as this position is regarded as final complete locking ensues by tightening the locking screw forming the fixing member 6 which for this purpose engages in a depression 5 of the catch 4.

In the embodiment described above the length of the setting screw 9 is chosen so that the setting screw reaches by its free end into the hollow interior of the second member 3 without coming into engagement with the opposite wall of the second member 3 so that there is no hindrance to the movement of the second member 3. As shown in the figures the second member 3 preferably has a recess 22 constructed in the form of an oblong hole which extends in its longitudinal direction parallel to the longitudinal axis of the space keeper and whose length and width are so constructed that the free end of the setting screw 9 with the threaded sleeve sliding thereon and the two shoulders 13 and 14 and the ends of the two lever arms 7 and 8 connected thereto in the back-and-forth movement shown in FIGS. 2 and 3 can move freely back and forth in the oblong hole. In this way it is achieved that the setting screw 9 may have a greater length by which means the travel of the threaded sleeve 10 is increased and hence the expandability of the two members or the space keeper is increased.

Figure 5:
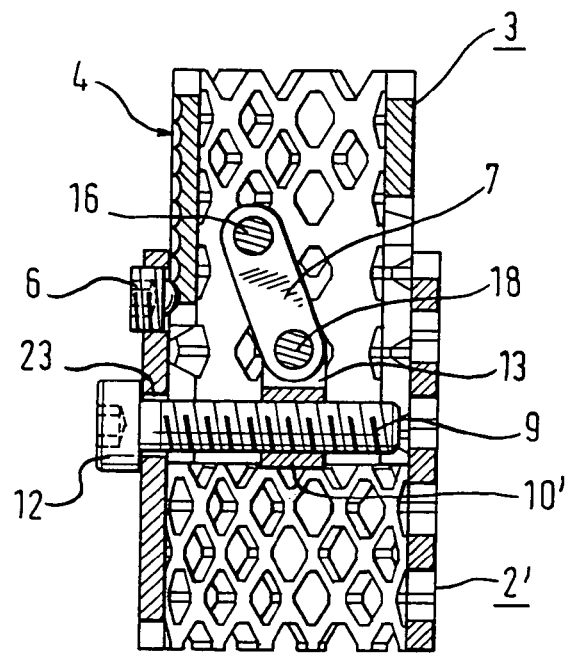
FIG. 5 a second embodiment in the extended position corresponding to the sectional illustration II/II.
Figure 6:
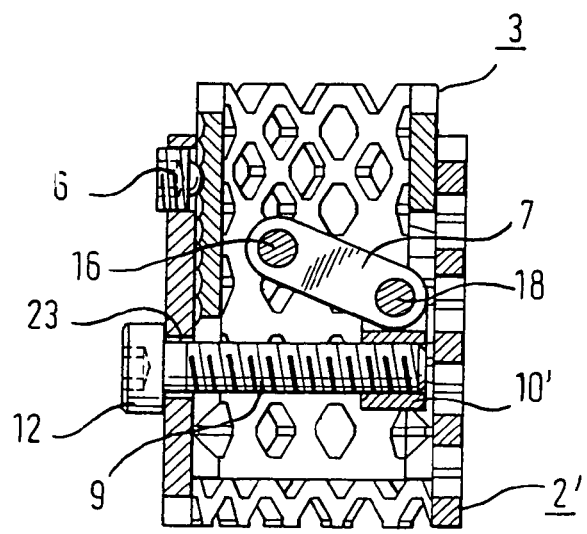
FIG. 6 the second embodiment in the contracted position.

In a modified embodiment shown in FIGS. 5 and 6 the second member 3, the setting screw 9, the first lever arm 7, the shoulder 13 and the two shafts 16 and 18 are constructed in the same way as the corresponding elements in the first embodiment.

In the second embodiment, instead of the oblong hole 11 a round hole 23 guiding the setting screw in the wall of the first member 2' is provided whose diameter is chosen so that the setting screw is guided rotatably in this hole. The threaded sleeve 10' has only one shoulder 13.

In operation adjustment between the compressed position shown in FIG. 6 and the expanded position shown in FIG. 5 is done as in the first embodiment by turning the setting screw 9 in such a way that the threaded sleeve 10' is screwed so far out of the most extreme position at the free end shown in FIG. 6 towards the head until expansion to a desired size has occurred or the lever 7 has moved almost into the vertical position. The concluding locking is done as in the first embodiment by tightening a fixing screw 6 in cooperation with the depressions 5 of the catch 4.

As may be seen in the figures the two walls of the first and second members are each constructed in such a way that they exhibit in the circumferential direction a plurality of diamond-shaped apertures 24. The free ends 25, 26 located opposite one another are as shown in the figures each of serrated construction whereby engagement in the adjoining vertebrae walls stabilizing against rotation is facilitated. The apertures in the wall facilitate ingrowing after the operation.

Figure 7:
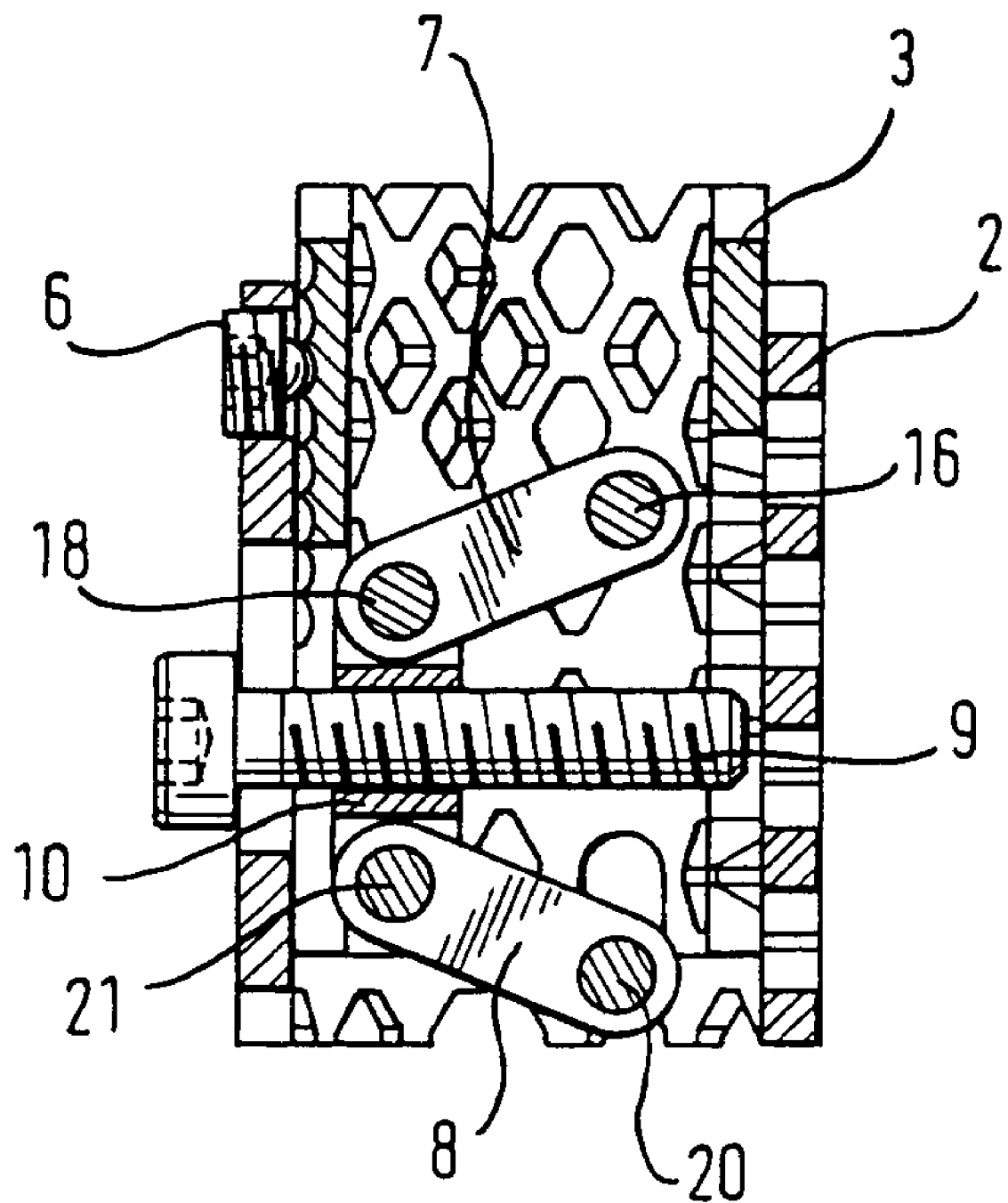
FIG. 7 a section through another embodiment.

In the embodiments described above the adjusting device of the setting screw 9, threaded sleeve 10 and lever arms 7, 8 or 7 is constructed in each case in such a way that the maximum extension occurs when the threaded sleeve 10 is moved to the maximum towards the head 12 and compressed to the furthest possible when the threaded sleeve 10 is at its greatest possible distance from the head 12. It is also possible, however, to reverse this device to the effect that the greatest extension possible is reached when the threaded sleeve 10 is at its greatest distance from the head 12. At the smallest distance from the head 12 the height has its lowest possible value. Such an embodiment is described in FIG. 7.

The invention claimed is:

1. A space keeper for insertion between two vertebrae, the space keeper having a longitudinal axis and a variable axial length and comprising:
    a sleeve-like first member having a first peripheral wall;
    a second member having a second peripheral wall and guided in the sleeve-like first member, the second member being moveable relative to the sleeve-like first member in an axial direction for adjusting an overall length of the space keeper;
    a lever connecting the sleeve-like first member and the second member, the lever comprising a first center of motion that is connected to the sleeve-like first member and a second center of motion that is connected to the second member;
    wherein movement of the second center of motion while connected to the second member relative to the first center of motion while the first center of motion is connected to the sleeve-like first member moves the second member relative to the sleeve-like first member to adjust the overall length of the space keeper; and
    wherein the second member further comprises a catch section extending in the axial direction on the second peripheral wall, the catch section comprising a plurality of depressions arranged adjacent to one another in the axial direction and bounding one another, the depressions facing the sleeve-like first member, the sleeve-like first member further comprising a fixing part that cooperates with the catch portion for locking the sleeve-like first member and the second member at a desired axial length of the space keeper.

2. A space keeper for insertion between two vertebrae, the space keeper having a longitudinal axis and a variable axial length and comprising:
    a sleeve-like first member having a first peripheral wall;
    a second member having a second peripheral wall and guided in the sleeve-like first member, the second member being moveable relative to the sleeve-like first member in an axial direction for adjusting an overall length of the space keeper; and
    a lever connecting the sleeve-like first member and the second member, the lever comprising a first center of motion that is connected to the sleeve-like first member and a second center of motion that is connected to the second member;
    wherein the sleeve-like first member further comprises an oblong hole in the first peripheral wall, the space keeper further comprising a setting screw having a free end and guided in the oblong hole, and a threaded sleeve guided on the setting screw, wherein the first center of motion is connected to the threaded sleeve.

3. The space keeper according to claim 2, wherein the peripheral walls of the first and second members have apertures distributed over the surface thereof.

4. The space keeper according to claim 2, the second member further comprising a longitudinal recess in the second peripheral wall opposite the oblong hole in the sleeve-like first member, the longitudinal recess extending parallel to the longitudinal axis of the space keeper, wherein the free end of the setting screw freely projects into the longitudinal recess.

5. The space keeper according to claim 2, wherein the lever has first and second arms, each arm connected to the threaded sleeve at a center of motion, the first arm further connected to the sleeve-like first member at the first center of motion, the second arm further connected to the second member at the second center of motion.

6. The space keeper according to claim 2, the second member further comprising a catch section extending in the axial direction on the second peripheral wall, the catch section comprising a plurality of depressions arranged adjacent to one another in the axial direction and bounding one another, the depressions facing the sleeve-like first member, the sleeve-like first member further comprising a fixing part that cooperates with the catch portion for locking sleeve-like first member and the second member at a desired axial length of the space keeper.

7. A space keeper for insertion between two vertebrae, the space keeper having a longitudinal axis and a variable axial length and comprising:
    a sleeve-like first member having a first peripheral wall;
    a second member having a second peripheral wall and guided in the sleeve-like first member, the second member being moveable relative to the sleeve-like first member in an axial direction for adjusting an overall length of the space keeper; and
    a lever connecting the sleeve-like first member and the second member, the lever comprising a first center of motion that is connected to the sleeve-like first member and a second center of motion that is connected to the second member;

wherein the sleeve-like first member further comprises a bore hole in the first peripheral wall, the space keeper further comprising a setting screw having a free end and guided in the bore hole, and a threaded sleeve guided on the setting screw, wherein the first center of motion is connected to the threaded sleeve.

8. The space keeper according to claim 7, wherein the peripheral walls of the first and second members have apertures distributed over the surface thereof.

9. The space keeper according to claim 7, the second member further comprising a longitudinal recess in the second peripheral wall opposite the bore hole in the sleeve-like first member, the longitudinal recess extending parallel to the longitudinal axis of the space keeper, wherein the free end of the setting screw freely projects into the longitudinal recess.

10. The space keeper according to claim 7, the second member further comprising a catch section extending in the axial direction on the second peripheral wall, the catch section comprising a plurality of depressions arranged adjacent to one another in the axial direction and bounding one another, the depressions facing the sleeve-like first member, the sleeve-like first member further comprising a fixing part that cooperates with the catch portion for locking sleeve-like first member and the second member at a desired axial length of the space keeper.

11. The space keeper according to claim 7, wherein the lever has first and second arms, each arm connected to the threaded sleeve at a center of motion, the first arm further connected to the sleeve-like first member at the first center of motion, the second arm further connected to the second member at the second center of motion.

* * * * *